(12) United States Patent
Richardson et al.

(10) Patent No.: US 9,658,142 B2
(45) Date of Patent: May 23, 2017

(54) METHOD AND APPARATUS FOR EXTRACTING AND COLLECTING SINGLE CELLS FROM FORMALIN-FIXED PARAFFIN EMBEDDED TISSUES

(71) Applicant: Arizona Board of Regents on behalf of Arizona State University, Scottsdale, AZ (US)

(72) Inventors: David Richardson, Chandler, AZ (US); Thai Tran, Phoenix, AZ (US); Dmitry Derkach, Gilbert, AZ (US); Colleen Ziegler, Tempe, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 15/099,121

(22) Filed: Apr. 14, 2016

(65) Prior Publication Data
US 2016/0305855 A1    Oct. 20, 2016

Related U.S. Application Data
(60) Provisional application No. 62/147,327, filed on Apr. 14, 2015.

(51) Int. Cl.
G01N 1/28 (2006.01)
B01L 3/00 (2006.01)

(52) U.S. Cl.
CPC ............ G01N 1/286 (2013.01); B01L 3/5027 (2013.01); *G01N 2001/2886* (2013.01)

(58) Field of Classification Search
CPC ............ G01N 1/286; G01N 2001/2886; B01L 3/5027
See application file for complete search history.

(56) References Cited

U.S. PATENT DOCUMENTS

| | | | |
|---|---|---|---|
| 6,156,576 A | 12/2000 | Allbritton et al. | |
| 2005/0048581 A1* | 3/2005 | Chiu ................ | B01L 3/502761 435/7.1 |
| 2005/0221339 A1* | 10/2005 | Griffiths ............. | B01F 5/0646 435/6.11 |
| 2014/0055853 A1* | 2/2014 | Corwin ............. | B01L 3/502715 359/391 |
| 2015/0005190 A1 | 1/2015 | Ciftlik et al. | |

FOREIGN PATENT DOCUMENTS

| WO | 2012162779 A1 | 12/2012 |
|---|---|---|
| WO | 2013074885 A1 | 5/2013 |
| WO | 2013130714 A1 | 9/2013 |
| WO | 2015048009 A1 | 4/2015 |

OTHER PUBLICATIONS

Kurth et al. Bridging the Gap: Towards Microfluidic Single Cell Analysis of In Vivo Stimulated Cells.17th International Conference on Miniaturized Systems for Chemistry and Life Sciences. Oct. 27-31, 2013, Freiburg, Germany. p. 1647-1649.*
Tangrea et al. Effect of Immunohistochemistry on Molecular Analysis of Tissue Samples: Implications for Microdissection Technologies. Journal of Histochemistry & Cytochemistry 59(6) 591-600.*
Antica, Mariastefania et al., "Gene expression in formalin-fixed parafin-embedded lymph nodes," Journal of Immunological Methods, vol. 359, 2010, pp. 42-46.
Author Unknown, "QIAsymphony® RNA Handbook: For purification of total RNA from animal and human cells and tissues using the QIAsymphony SP," QIAGEN Sample & Assay Technologies, Feb. 2013, 44 pages.
Author Unknown, "Thermo Scientific Cell and Protein Isolation Technical Handbook: Tools and reagents for optimal protein extraction," Thermo Fisher Scientific, 2015, 72 pages.
Böhm, Malte et al., "Microbeam MOMeNT: Non-Contact Laser Microdissection of Membrane-Mounted Native Tissue," American Journal of Pathology, vol. 151, No. 1, Jul. 1997, pp. 63-67.
Emmert-Buck, Michael R. et al., "Laser Capture Microdissection," Science, vol. 274, Nov. 8, 1996, pp. 998-1001.
Fend, Falko et al., "Laser capture microdissection in pathology," Journal of Clinical Pathology, vol. 53, 2000, pp. 666-672.
Hudock, Teresa A. et al., "A novel microdissection approach to recovering *Mycobacterium tuberculosis*-specific transcripts from formalin fixed paraffin embedded lung granulomas," Journal of Visualized Experiments, vol. 88, 2014, 12 pages.
Körbler, Tajana et al., "A simple method for RNA isolation from formalin-fixed and paraffin-embedded lymphatic tissues," Experimental and Molecular Pathology, vol. 74, 2003, pp. 336-340.
Okello, John B.A. et al., "Comparison of methods in the recovery of nucleic acids from archival formalin-fixed paraffin-embedded autopsy tissues," Analytical Biochemistry, vol. 400, 2010, pp. 110-117.
Perkel, Jeffrey M., "Working with FFPE Tissue," Biocompare Editorial Article, Feb. 17, 2010 [retrieved on Mar. 22, 2016], 7 pages, Retrieved from: www.biocompare.com/Editorial-Articles/41751-Working-with-FFPE-Tissue/.
Roberts, Lisa et al., "Identification of methods for use of formalin-fixed, paraffin-embedded tissue samples in RNA expression profiling," Genomics, vol. 94, 2009, pp. 341-348.
Rudd, Edwin et al., "Active paraffin removal from FFPE tissues with Adaptive Focused Acoustics," Covaris, Application Note, Oct. 2013, 3 pages.

(Continued)

*Primary Examiner* — Taeyoon Kim
(74) *Attorney, Agent, or Firm* — Withrow & Terranova, P.L.L.C.; Vincent K. Gustafson

(57) ABSTRACT

Methods and apparatuses are provided for extraction and collection of sets of one or more cells from a formalin-fixed paraffin embedded tissue sample. A laser is used to remove sets of one or more cells from an immobilized sample within a microfluidic device, and a fluid flow element washes the removed set of one or more cells away from the immobilized sample, preferably to be collected in a downstream sample collection device. Morphological and/or positional information may be preserved to permit at least one technique (e.g., amplification, sequencing, and/or analytical, optionally performed after cells are lysed downstream of the microfluidic device) to be related to the original spatial location of the set of one or more cells in the immobilized sample.

21 Claims, 10 Drawing Sheets

(56) References Cited

OTHER PUBLICATIONS

Srivastava, Prashant K. et al., "A cut-off based approach for gene expression analysis of formalin-fixed and paraffin-embedded tissue samples," Genomics, vol. 91, 2008, pp. 522-529.

Vandewoestyne, Mado et al., "Laser capture microdissection: Should an ultraviolet or infrared laser be used?" Analytical Biochemistry, vol. 439, No. 2, Aug. 15, 2013, pp. 88-98.

Von Ahlfen, Silke et al., "Determinants of RNA Quality from FFPE Samples," PLoS ONE, vol. 2, No. 12, Dec. 2007, 7 pages.

Verified Amended Complaint filed Mar. 14, 2016 in *Deirdre Meldrum* vs. *Arizona Board of Regents et al.*, in Case No. CV2016-001614 in the Superior Court for the State of Arizona in and for the County of Maricopa, including allegations concerning "Interference with Intellectual property" (relating to U.S. Appl. No. 62/147,327 based on Invention Disclosure M15-170L) at pp. 19-21, paragraphs Nos. 68-75, 33 pages.

Scicchitano, Marshall, S., et al., "Protein Extraction of Formalin-fixed, Paraffin-embedded Tissue Enables Robust Proteomic Profiles by Mass Spectrometry," Journal of Histochemistry and Cytochemistry, Sep. 2009, vol. 57, Issue 9, The Histochemical Society, Inc., pp. 849-860.

Vaganova, A.N., "Histotechnical solutions for quality improvement of nucleic acid specimens extracted from paraffin blocks," Geny & Kletki, Tom IX, Issue 2, 2014, 13 pages.

International Search Report and Written Opinion for PCT/US2016/027483, mailed Jul. 14, 2016, 7 pages.

\* cited by examiner

Arcturus PixCell II IR LCM         PALM Zeiss UV LCM
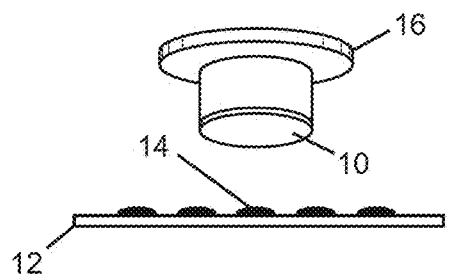
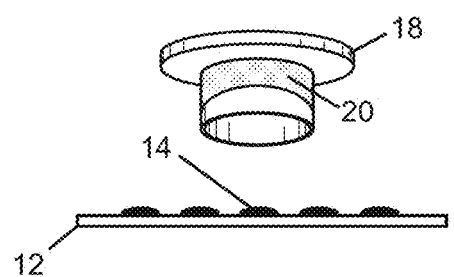
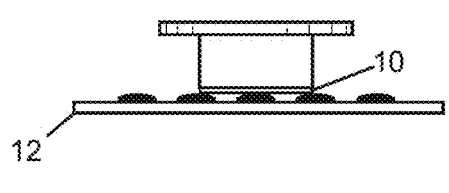
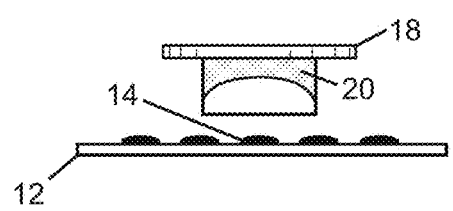
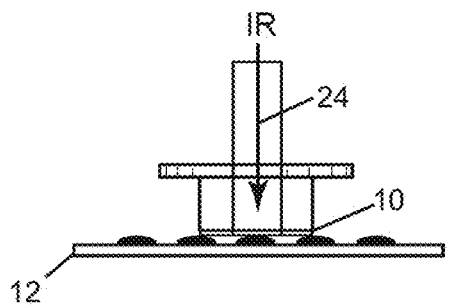
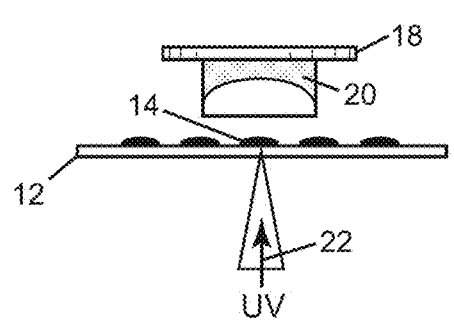
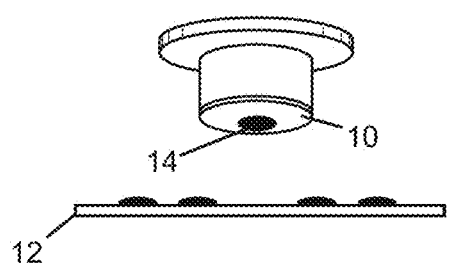
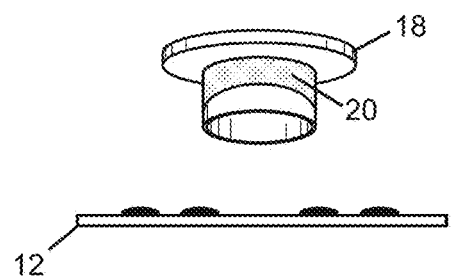
*FIG. 1A (RELATED ART)*         *FIG. 1B (RELATED ART)*

FFPE Sample

Molecular Analysis qRT-PCR
RNA Seq
DNA Seq
NGS

Results

US 9,658,142 B2

METHOD AND APPARATUS FOR EXTRACTING AND COLLECTING SINGLE CELLS FROM FORMALIN-FIXED PARAFFIN EMBEDDED TISSUES

CROSS-REFERENCE TO RELATED APPLICATION(S)

This application claims the benefit of U.S. Provisional Patent Application No. 62/147,327 filed on Apr. 14, 2015, with the disclosure of such application being hereby incorporated by reference herein.

GOVERNMENT RIGHTS IN INVENTION

This invention was made with government support under R21 CA174412 awarded by the National Institutes of Health. The government has certain rights in the invention.

TECHNICAL FIELD

This disclosure concerns methods for extracting and collecting single cells from formalin-fixed paraffin embedded tissues, and apparatuses utilizing microfluidic devices and laser energy enabling performance of such methods.

BACKGROUND

Formalin-fixed paraffin embedded (FFPE) samples are derived from tissues (usually suspected tumor samples obtained by biopsy or dissection) that are fixed with formalin to preserve the cytoskeletal and protein structure and then embedded in a type of paraffin wax. FFPE is well-established and is widely used for histological analysis of clinical and research tissue samples utilized by pathologists for diagnostic purposes and by researchers. FFPE has been the preferred method for preserving tissue samples because it allows for extended room temperature storage of tissues while maintaining histopathology integrity. DNA, RNA, and proteins have been successfully extracted from bulk FFPE samples.

Formalin serves to cross-link proteins thus preserving the structural integrity of the cells and permitting the cells to be examined for histological, pathological, or cytological studies. FFPE samples are commonly sliced on a microtome, which is an instrument used to prepare very thin slices of a sample.

A conventional method for removing a cell or a small group of cells from a FFPE sample is laser capture microdissection (LCM). LCM combines microscopy with laser beam technology and allows targeting of specific cells or tissue regions that need to be separated from others. Two conventional LCM systems are schematically illustrated in FIGS. 1A and 1B. FIG. 1A schematically illustrates the PixCell II infrared LCM system commercialized by Arcturus Engineering (Mountain View, Calif., US), which utilizes a thin transparent thermoplastic film 10 (supported by a collector 16) that is placed over a tissue section supported by a glass slide 12. Cells of interest 14 are selectively adhered to the film 10 with a fixed-position, short duration, focused IR laser pulse 24. The adherence of the cells of interest 14 to the film 10 exceeds the adhesion to the glass slide 12, thereby allowing selective removal of cells of interest 14. Such cells of interest 14 are detached by lifting the film 10, and are transferred to an Eppendorf microcentrifuge tube (not shown) containing a buffer solution for isolation of DNA or RNA. FIG. 1B schematically illustrates the Palm Zeiss ultraviolet LCM system commercialized by P.A.L.M. Microlaser Technologies AG (Bernried, Germany). A highly focused UV laser beam 22 is used to cut out cells or regions of interest 14 from a tissue sample supported by a glass slide 12. By increasing the power of the laser, desired cells of interest 14 are ejected against gravity into a collection device (a "cap") 18 containing a lysis buffer 20.

LCM can cut single cells from planar (two-dimensional) FFPE tissues, but cannot remove cells individually that are stacked on top of each other. In other words, LCM lacks resolution in the z-direction. LCM methods also do not lend themselves to high throughput since each cut cell must be placed into an Eppendorf microcentrifuge tube and subsequently handled.

The art continues to seek improved methods and apparatuses for extracting and collecting single cells or small groups of cells from FFPE tissue samples to overcome limitations associated with conventional methods and apparatuses. Aspects of this disclosure address shortcomings associated with conventional systems and methods.

SUMMARY

Aspects of this disclosure relate to methods and apparatuses for extraction and collection of sets of one or more cells from a FFPE tissue sample and preserving tracking of morphological and/or positional information of the removed sets relative to the FFPE tissue sample. Methods and apparatuses disclosed herein utilize a laser to remove sets of one or more cells from an immobilized sample within the interior of a microfluidic device, and at least one fluid flow element to wash the removed sets of one or more cells away from the immobilized sample—preferably to be collected in a sample collection device arranged downstream of the microfluidic device. Morphological and/or positional information may be preserved to permit at least one technique (e.g., an amplification technique, a sequencing technique, or an analytical technique) to be related to the original spatial location of the set of one or more cells in the immobilized sample. In certain embodiments, any suitable lysing technique known in the art may be used downstream of the microfluidic device to extract cellular contents and permit at least one of the above-mentioned techniques to be performed.

In certain aspects, the disclosure relates to a method for extracting at least a first set of one or more cells from a sample, the method including: directing laser energy through a surface of a microfluidic device to impinge on at least a first portion of the sample immobilized within a chamber of the microfluidic device and to remove the at least a first set of one or more cells from the sample by laser ablation, wherein the sample includes a modified FFPE sample from which paraffin has been removed; and washing the removed at least a first set of one or more cells from the microfluidic device by flowing at least one liquid through at least a portion of the microfluidic device. In certain embodiments, the sample includes a thickness in a range of at least 3 microns, or from 3 microns to about 10 microns, or from about 5 microns to about 10 microns. In certain embodiments, the sample may comprise a greater thickness, such as in a range of at least about 3 microns, 5 microns, 10 microns, 20 microns, 35 microns, 50 microns, 75 microns, or 100 microns (with one or more of the preceding values optionally being bounded by an upper thickness threshold of up to 50 microns, up to 100 microns, up to 150 microns, or up to 200 microns). Other sample thickness ranges or subranges of the preceding thresholds may be used. In certain embodiments, the method further includes removing paraffin wax from a FFPE sample retained on a cover layer of the microfluidic device to yield the modified FFPE sample, and affixing the cover layer to at least one microfluidic device layer to yield the sample immobilized within the microfluidic device. In certain embodiments, the method further includes collecting the removed at least a first set of one or more cells in a sample collection element. In certain embodiments, the method further includes storing information representative of morphology or position, relative to the immobilized sample, of the removed at least a first set of one or more cells. In certain embodiments, the method further includes performing at least one technique selected from an amplification technique, a sequencing technique, or an analytical technique, utilizing the removed at least a first set of one or more cells. In certain embodiments, the method further includes at least one of correlating, associating, or storing results of the at least one technique with the information representative of morphology or position. In certain embodiments, said flowing of at least one liquid through the at least a portion of the microfluidic device includes flowing a plurality of discrete plugs of a first liquid and a second liquid through the at least a portion of the microfluidic device, wherein the first liquid is substantially immiscible with the second liquid under flow conditions within the microfluidic device. In certain embodiments, the method further includes detecting the plurality of discrete plugs of the first liquid and the second liquid, and capturing or manipulating the removed at least a first set of one or more cells responsive to said detecting. In certain embodiments, the method further includes collecting the removed at least a first set of one or more cells in a multi-well or multi-chamber sample collection element. In certain embodiments, the method further includes impinging laser energy on at least a second portion of the sample immobilized within the microfluidic device to remove at least a second set of one or more cells from the sample by laser ablation; and washing the removed at least a second set of one or more cells from the microfluidic device by flowing the at least one liquid through the at least a portion of the microfluidic device. In certain embodiments, the method further includes performing an optical detection technique on the removed at least a first set of one or more cells through an optical detection region arranged downstream of the chamber. In certain embodiments, such optical detection region is arranged in or on the microfluidic device.

In certain aspects, the disclosure relates to an apparatus for extracting at least a first set of one or more cells from an immobilized sample, the apparatus including: a microfluidic device interface arranged to receive, and provide fluidic connections to, a microfluidic device; a laser arranged to direct laser energy through a surface of a microfluidic device received by the microfluidic device interface and impinge on at least a first portion of a sample immobilized within a chamber the microfluidic device for removal of at least a first set of one or more cells from the sample by laser ablation; a position control element arranged to effect relative translation between the microfluidic device interface and the laser; at least one liquid flow control element arranged to cause at least one liquid to flow through at least a portion of the microfluidic device and wash the removed at least a first set of one or more cells from the chamber; a dispenser arranged to dispense the removed at least a first set of one or more cells into at least one sample collection element positioned downstream of the microfluidic device. In certain embodiments, the apparatus further includes a memory arranged to store information representative of morphology or position, relative to the immobilized sample, of the removed at least a first set of one or more cells. In certain embodiments, the apparatus further includes a translation stage arranged to effect relative movement between the dispenser and the at least one sample collection element. In certain embodiments, the apparatus further includes at least one sample collection element includes a multi-well or multi-chamber sample collection element.

In certain aspects, the disclosure relates to a microfluidic device including: at least one fluid inlet port; at least one fluid outlet port; a sample chamber arranged between the at least one fluid inlet port and the at least one fluid outlet port, wherein the sample chamber is bounded along one surface by a cover layer; and a modified FFPE sample retained on the cover layer and within the sample chamber, wherein the modified FFPE sample includes a FFPE sample from which paraffin has been removed; wherein at least one surface bounding the sample chamber is substantially transmissive of laser energy. In certain embodiments, the modified FFPE sample includes a thickness of at least about 3 microns, or from about 3 microns to about 10 microns, or from about 5 microns to about 10 microns. In other embodiments, the sample may comprise a greater thickness, such as in a range of at least about 3 microns, 5 microns, 10 microns, 20 microns, 35 microns, 50 microns, 75 microns, or 100 microns (with one or more of the preceding values optionally being bounded by an upper thickness threshold of up to 50 microns, up to 100 microns, up to 150 microns, or up to 200 microns). In certain embodiments, the at least one fluid inlet port includes a first fluid inlet port arranged to receive a first liquid and a second fluid inlet port arranged to receive a second liquid. In certain embodiments, the sample chamber includes at least one of a height dimension and a width dimension of less than about 500 microns, less than about 300 microns, less than about 250 microns, less than about 200 microns, less than about 100 microns, less than about 50 microns, or another threshold recited herein. In certain embodiments, the microfluidic device may further comprise an optical detection region in or on the microfluidic device and arranged downstream of the sample chamber.

In certain aspects, the disclosure relates to a method for extracting and collecting multiple sets of one or more cells from a sample, the method including: directing laser energy from a laser through a surface of a microfluidic device to impinge on a first portion of the sample immobilized within a chamber of the microfluidic device and remove a first set of one or more cells from the sample by laser ablation, wherein the sample comprises a modified FFPE sample from which paraffin has been removed; washing the removed first set of one or more cells from the microfluidic device by flowing at least one liquid through the chamber; collecting the first set of one or more cells in at least one sample collection element disposed downstream of the microfluidic device; directing laser energy through the surface of a microfluidic device to impinge on a second portion of the sample immobilized within the chamber and to remove a second set of one or more cells from the sample by laser ablation; washing the removed second set of one or more cells from the microfluidic device by flowing at least one liquid through the chamber; and collecting the second set of one or more cells in the at least one sample collection element disposed downstream of the microfluidic device. In certain embodiments, the method further includes effecting relative movement between the laser and the microfluidic device (e.g., after collecting the first set of one or more cells and before directing laser energy through the surface of the microfluidic device to impinge on the second portion of the sample). In certain embodiments, the sample includes a thickness of at least about 3 microns, or in a range of from about 3 microns to about 10 microns, or from about 5 microns to about 10 microns. In other embodiments, the sample may comprise a greater thickness, such as in a range of at least about 3 microns, 5 microns, 10 microns, 20 microns, 35 microns, 50 microns, 75 microns, 100 microns (with one or more of the preceding values optionally being bounded by an upper thickness threshold of up to 50 microns, up to 100 microns, up to 150 microns, or up to 200 microns). In certain embodiments, the method further includes removing paraffin wax from a FFPE sample retained on a cover layer of the microfluidic device to yield the modified FFPE sample, and affixing the cover layer to at least one microfluidic device layer to yield the sample immobilized within the microfluidic device. In certain embodiments, the method further includes storing information representative of morphology or position, relative to the immobilized sample, of the removed first set of one or more cells, and storing information representative of morphology or position, relative to the immobilized sample, of the removed second set of one or more cells. In certain embodiments, the method further includes performing at least one first technique independently selected from an amplification technique, a sequencing technique, or an analytical technique, utilizing the removed first set of one or more cells; performing at least one second technique independently selected from an amplification technique, a sequencing technique, or an analytical technique, utilizing the removed second set of one or more cells; performing at least one of correlating, associating, or storing results of the at least one first technique with the information representative of morphology or position of the removed first set of one or more cells; and performing at least one of correlating, associating, and storing results of the at least one second technique with the information representative of morphology or position of the removed second set of one or more cells. In certain embodiments, said flowing of at least one liquid through the chamber includes flowing a plurality of discrete plugs of a first liquid and a second liquid through the chamber, wherein the first liquid is substantially immiscible with the second liquid under flow conditions within the microfluidic device. In certain embodiments, the method further includes detecting the plurality of discrete plugs of the first liquid and the second liquid, and capturing or manipulating at least one of the first removed set of one or more cells or the second removed set of one or more cells responsive to said detecting.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

FIG. 1A schematically illustrates operation of a PixCell II infrared laser capture microdissection system.

FIG. 1B schematically illustrates operation of a Palm Zeiss ultraviolet laser capture microdissection system.

DETAILED DESCRIPTION

Figure 2A:
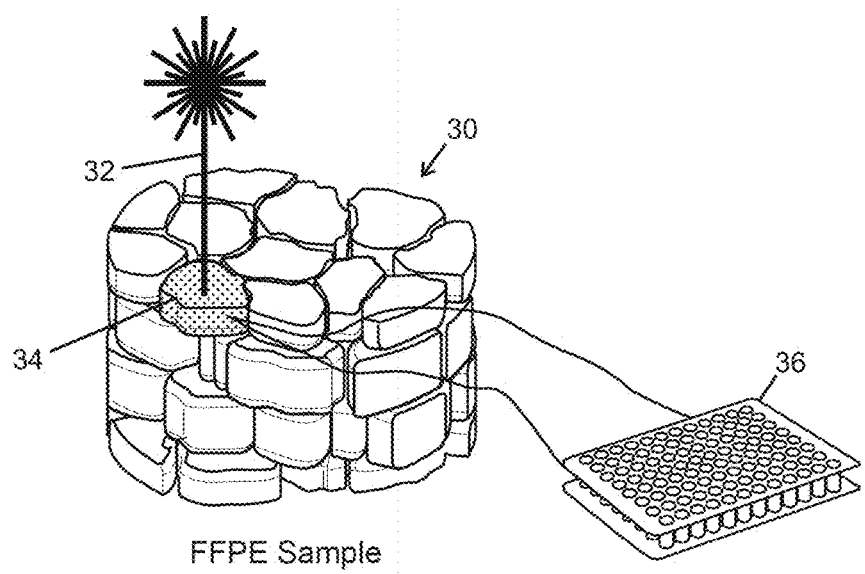
FIG. 2A schematically illustrates a cell of a three-dimensional FFPE sample being irradiated by a laser beam, and a downstream sample collection element (e.g., 96-well plate) arranged to receive an ablated set of one or more cells by washing from a collection device containing the sample.

Aspects of this disclosure relate to methods and apparatuses for extraction and collection of sets of one or more cells from a FFPE tissue sample and preservation of tracking of morphological and/or positional information of the removed sets relative to the FFPE tissue sample. Methods and apparatuses disclosed herein utilize a laser to remove sets of one or more cells from an immobilized sample within the interior of a microfluidic device, and at least one fluid flow element to wash the removed sets of one or more cells away from the immobilized sample—preferably to be collected in a sample collection device arranged downstream of the microfluidic device. Morphological and/or positional information of information may be preserved to permit at least one technique (e.g., an amplification technique, a sequencing technique, or an analytical technique) to be related to the original spatial location of the set of cells in the immobilized sample.

As noted previously, DNA/RNA and proteins have been successfully extracted from FFPE samples, but FFPE lacks general resolution of the single cell and completely lacks resolution in a third spatial dimension (i.e., the z-direction). Enabling 3D resolution allows the correlation of morphology to information like gene expression which may illuminate disease mechanisms and treatment efficacies, and facilitate a transition toward personalized medicine.

In certain embodiments, a FFPE sample is prepared on a light-transmissive glass slide (or alternatively on a polymeric slide) and then subjected to treatment to remove paraffin wax and to rehydrate the sample. The resulting modified FFPE sample can include full, partial, or no reverse crosslinking. Preferably, paraffin removal results in removal of at least 80%, at least 90%, at least 95%, or another threshold amount, of paraffin originally present in the FFPE sample.

Various techniques may be used for paraffin removal. In certain embodiments, an organic solvent such as xylene, CitriSolv, or mineral oil may be used to dissolve paraffin. In other embodiments, active paraffin removal may be accomplished by emulsification using adaptive focused acoustics (AFA) technology using focused untrasonicators such as disclosed by Covaris, Inc. (Woburn, Mass., USA) in an October 2013 application note entitled "Active paraffin removal from FFPE tissues with Adaptive Focused Acoustics."

In certain embodiments, portions of a microfluidic device may be prefabricated and arranged to receive a glass or polymeric slide including a surface on which a FFPE sample (preferably a modified FFPE sample) is retained. The slide to which the sample is mounted may be mounted to one or more other prefabricated microfluidic device layers to cause the immobilized sample to be retained within the interior of a microfluidic device. One or more other prefabricated microfluidic device layers may define fluid ports, vias, channels, and/or chambers that may be enclosed by addition of a cover layer. Preferably, one or more prefabricated microfluidic device layers may define an open channel or chamber arranged to receive the immobilized sample. At least one surface of a channel or chamber arranged to receive an immobilized FFPE (or modified FFPE) sample is substantially transmissive of laser energy of a desired wavelength, to permit laser energy to be transmitted through at least one surface of the microfluidic device to impinge on at least one region of the immobilized sample within the device.

In certain embodiments, a microfluidic device disclosed herein may include at least one channel or chamber having at least one dimension (e.g., a height dimension and/or a width dimension) of less than about 500 microns, less than about 300 microns, less than about 250 microns, less than about 200 microns, less than about 150 microns, less than about 100 microns, less than about 50 microns, or another threshold recited herein.

Traditionally, microfluidic devices have been fabricated from rigid materials such as silicon or glass substrates using surface micromachining techniques to define open channels and then affixing a cover to a channel-defining substrate to enclose the channels. Various methods may be used to fabricate microfluidic devices described herein. Such techniques may include machining, micromachining (including, for example, photolithographic wet or dry etching), molding, micromolding, LIGA, soft lithography, embossing, stamping, surface deposition, and/or combinations thereof to define apertures, channels, or chambers in one or more surfaces of a material or that penetrate through a material.

In certain embodiments, microfluidic devices may be constructed utilizing stencil fabrication, which includes the joining (e.g., via adhesion, lamination, or other means) of at least three device layers including at least one stencil layer or sheet defining one or more microfluidic channels and/or other microstructures. A stencil layer is preferably substantially planar in character and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Selection of particular materials for a desired application depends on numerous factors including: the types, concentrations, and residence times of substances (e.g., solvents, reactants, and products) present in regions of a device; temperature; pressure; pH; and optical properties. For instance, particularly desirable polymers include polycarbonates, acrylics, polyesters, polyolefins, polyimides, and vinyl-based polymers. As noted previously, however, at least one layer bounding a sample chamber should be transmissive of laser light, and preferably should also be transmissive of visible light to permit viewing or visualization of a sample chamber before and during laser ablation.

Various means may be used to seal or bond layers of a device together. For example, adhesives may be used. In one embodiment, one or more layers of a device may be fabricated from polymeric material including adhesive material pre-applied to one or both major surfaces thereof, although other methods of adhering stencil layers may be used. Portions of an adhesive-bearing layer (which may include one or more removable carrier layers covering adhesive surfaces) of desired shape and dimensions can be cut and removed to form channels, chambers, and/or apertures. An adhesive-bearing stencil layer can then be placed on a supporting substrate with an appropriate cover layer, between other stencil layers, or between layers of other materials. In certain embodiments, adhesives compatible with PCR amplification (including thermal cycling) may be used.

Suitable stencil layer materials include but are not limited to polyesters, polycarbonates, polytetrafluoroethlyenes, polypropylenes, and polyimides carriers. Adhesives associated with stencil materials may have various methods of curing, including curing by pressure, temperature, or chemical or optical interaction. The thickness of the stencil carrier and adhesives portions may be varied. In certain embodiments, one or more stencil layers may be fabricated of Melinex® PET 2 mil (50 micron) thickness self-adhesive film (available from the Fralock Division of Lockwood Ind. Inc., San Carlos, Calif.).

Although stencil fabrication desirably permits rapid prototyping of new device designs, in certain embodiments microfluidic structures may be fabricated via micromolding. In certain embodiments, one or more molds may be fabricated defining various features corresponding to channels, chambers, ports, and/or vias. Thereafter, molten or other liquid-containing material may be supplied to the mold(s), and such material may be cured or otherwise hardened. Upon release from the mold(s), the resulting device layer(s) may be used alone or in combination (e.g., after joining) to receive a cover (e.g., a glass or polymeric slide) on which a FFPE (or preferably a modified FFPE) sample is immobilized, with the cover serving to enclose at least one channel or chamber of a microfluidic device in which the sample is retained.

If desired, microfluidic device layers may be directly bonded without using adhesives to provide high bond strength and eliminate potential compatibility problems between such adhesives and solvents and/or samples. For example, solvent bonding or adhesiveness thermal bonding (using elevated heat and/or pressure) may be used. Other techniques may also be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other coupling methods may be used.

In certain embodiments, an alignment fixture may cooperate with one or more alignment features included in or on microfluidic device layers to facilitate alignment between layers when such layers are stacked together.

Following fabrication of a microfluidic device containing a FFPE (or modified FFPE) tissue sample, single cell extraction from the tissue sample is achieved by directing laser energy through a surface of the microfluidic device to impinge on the sample. Such impingement mechanically reverse-crosslinks the irradiated area and ablates (or separates) a set of one or more cells. After such separation, the set of one or more cells may be washed away from a sample chamber through a microfluidic channel and deposited in a suitable sample collection device (e.g., a standard 96 well plate) to permit manipulation (e.g., amplification, sequencing, and/or analysis) of the cellular contents. In certain embodiments, manipulation of cellular contents includes one or more immunohistochemistry techniques (which combine anatomical, immunological and biochemical techniques to identify discrete tissue components by the interaction of target antigens with specific antibodies tagged with a visible label). In certain embodiments, sets of one or more cells may be tagged with magnetic beads or other markers upon or after removal from a modified FFPE sample.

Various types of laser energy may be used to perform ablation. In certain embodiments, a two photon infrared laser having a wavelength of 800 nm may be used. A two photon laser is preferred to provide high resolution. Infrared laser energy is preferred in certain embodiments to reduce absorption by target material. Laser energy is preferably pulsed. Duration and number of laser pulses may be adjusted to accomplish removal of one or more cells from a modified FFPE sample immobilized within a microfluidic device. In certain embodiments, pulse trains may be delivered to the tissue at various power intensities and durations as needed while the tissue is exposed to liquid flow through the sample chamber. In certain embodiments, a 50 millisecond train of laser pulses may be used and repeated as desired. Other pulse train durations may be used, as will be recognized by one skilled in the art.

In certain embodiments, a microfluidic device is arranged to be received by a microfluidic device interface that provides fluidic connections to the microfluidic device. Preferably, the microfluidic device interface is compatible with a microscope or other imaging apparatus to permit at least a sample-containing portion of the microfluidic device to be viewed or imaged (e.g., using visible light) before and during laser ablation. In certain embodiments, a position control element (e.g., x-y translation apparatus) may be arranged to effect relative translation between the microfluidic device interface and the laser, such as by moving either the microfluidic device interface or the laser. Such translation may permit a laser beam to be focused on one area of interest on the sample, and then focused on another area of interest on the sample, and so on. In certain embodiments, such as may be suitable for research use, a joystick, tablet, or other user input element may be used to control relative translation between the microfluidic device interface and the laser, and laser firing (e.g., pulsing) may be controlled with one or more other user input elements such as a button, foot pedal, or the like. In other embodiments, such as may be suitable for high-throughput commercial use, a translation and laser pulsing pattern may be pre-defined or defined by a user, and relative translation between the microfluidic device interface and the laser as well as laser pulsing may be automated (e.g., controlled via computer hardware or computer hardware in combination with software) according to such pattern. In certain embodiments, such relative translation may include rastering, by which an entire tissue sample or portion thereof may be subject to laser irradiation, followed by relative translation and laser irradiation for separation of one or more cells and removal by washing, followed by relative translation and laser irradiation for separation of one or more cells and removal by washing, and so on.

In certain embodiments, when laser irradiation is performed, information indicative of morphology and/or position of each set of one or more cells to be removed from a sample is recorded in a memory. Such morphological and/or positional information may be preserved to permit at least one technique (e.g., an amplification technique, a sequencing technique, or an analytical technique) to be related to the original spatial location of the set of cells in the immobilized sample. In this manner, correlation between analytical results and position may be established. If desired, such information may be used to reconstruct a virtual model or other representation of the original FFPE sample in which analytical results or other properties specific to individual sets of one or more cells may be visualized. In certain embodiments, an output may embody a "heat map" of expression of a particular gene.

Figure 2B:
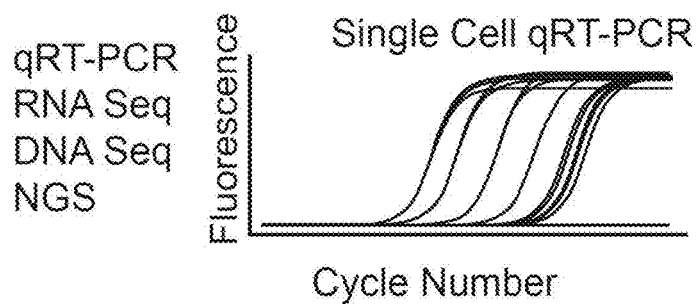
FIG. 2B is a representative chart derivable from a molecular analysis step that may be performed on cells separated from a FFPE sample.
Figure 2C:
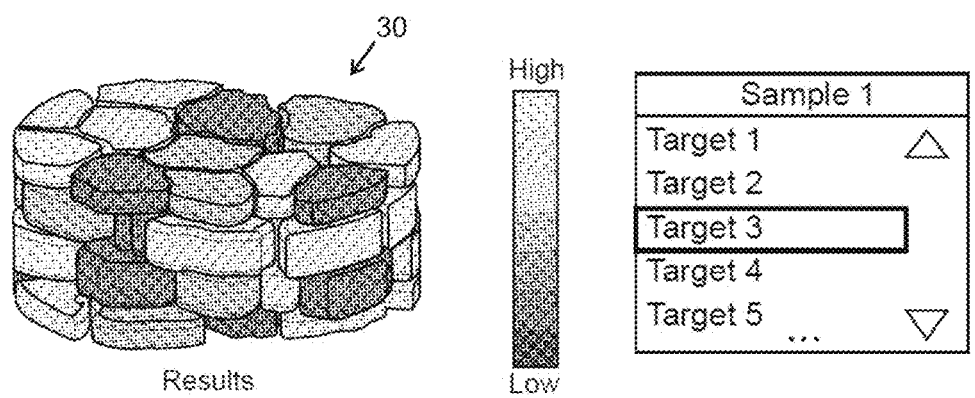
FIG. 2C schematically illustrates the three-dimensional FFPE sample of FIG. 2A with grayscale-coded activity or expression information following sequential ablation of all cells and molecular analysis, and further illustrates a table in which analytical data may be stored for different targets (e.g., cells) of the FFPE sample.

FIG. 2A schematically illustrates a cell 34 of a three-dimensional FFPE sample 30 being irradiated by a laser beam 32, and a downstream sample collection element (e.g., 96-well plate) 36 arranged to receive an ablated set of one or more cells (e.g., cell 34) by washing (e.g., from a microfluidic device containing the sample). FIG. 2B schematically illustrates a chart derivable from a molecular analysis step that may be performed on cells separated from a FFPE sample. FIG. 2C schematically illustrates the three-dimensional FFPE sample 30 of FIG. 2A with grayscale-coded activity or expression information (e.g., a "heat map") following sequential ablation of all cells and the analysis represented in FIG. 2B. FIG. 2C further illustrates a table in which analytical data may be stored for different targets (e.g., cells) of the FFPE sample. FIGS. 2A-2C show that methods disclosed herein enable morphological information to be preserved in three dimensions.

Figure 3:
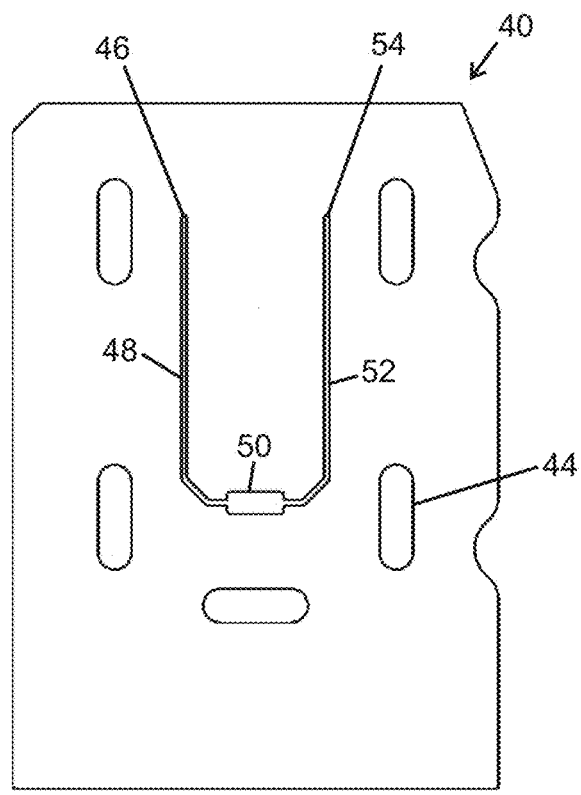
FIG. 3 is a top plan view of a microfluidic device including a buffer/reagent inlet, a cellular contents outlet, and a tissue sample chamber arranged between the inlet and the outlet, according to one embodiment of the present disclosure.

FIG. 3 is a top plan view of a microfluidic device 40 including a buffer/reagent inlet 46, a cellular contents outlet 54, and a tissue sample chamber 50 arranged between the inlet 46 and the outlet 54. A microfluidic upstream channel 48 is arranged between the inlet 46 and the sample chamber 50, and a microfluidic downstream channel 52 is arranged between the sample chamber 50 and the outlet 54. Five oblong peripheral alignment openings 44 are arranged to permit alignment of various layers of the microfluidic device 40 during fabrication with raised protrusions of an alignment fixture (such as the raised protrusions 84 and fixture 80 shown in FIG. 4B). A modified FFPE tissue sample is immobilized in the sample chamber 50. Buffer and/or reagent liquids may be supplied to the sample chamber 50 through the buffer/reagent inlet 46 and the upstream channel 48, and upon laser ablation, such liquid(s) may wash a set of one or more cells from the sample chamber 50 through the downstream channel 52 to the cellular contents outlet 54, to be received by one or more sample collection elements (e.g., such as the sample collection element 36 shown in FIG. 2A).

Figure 4A:
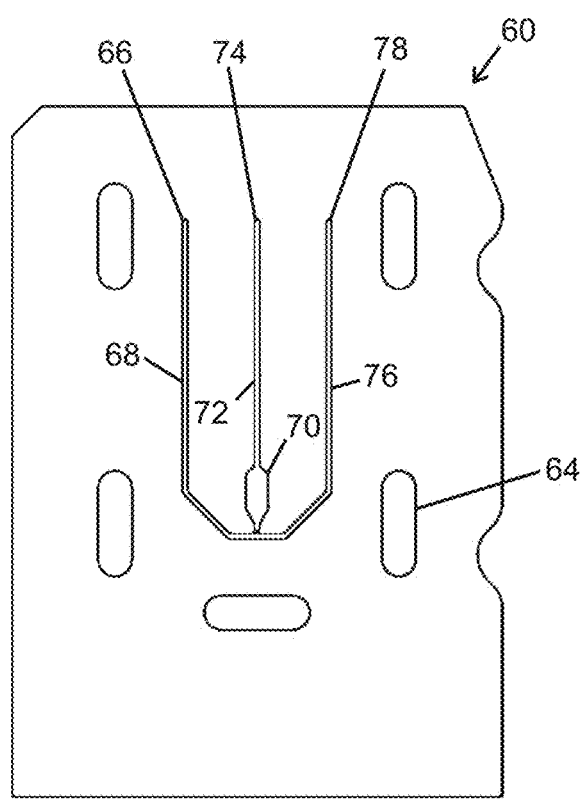
FIG. 4A is a top plan view of another microfluidic device that includes an oil inlet, a buffer/reagent inlet, a cellular contents outlet, and a tissue sample chamber arranged between the inlets and the outlet, according to one embodiment of the present disclosure.
Figure 4B:
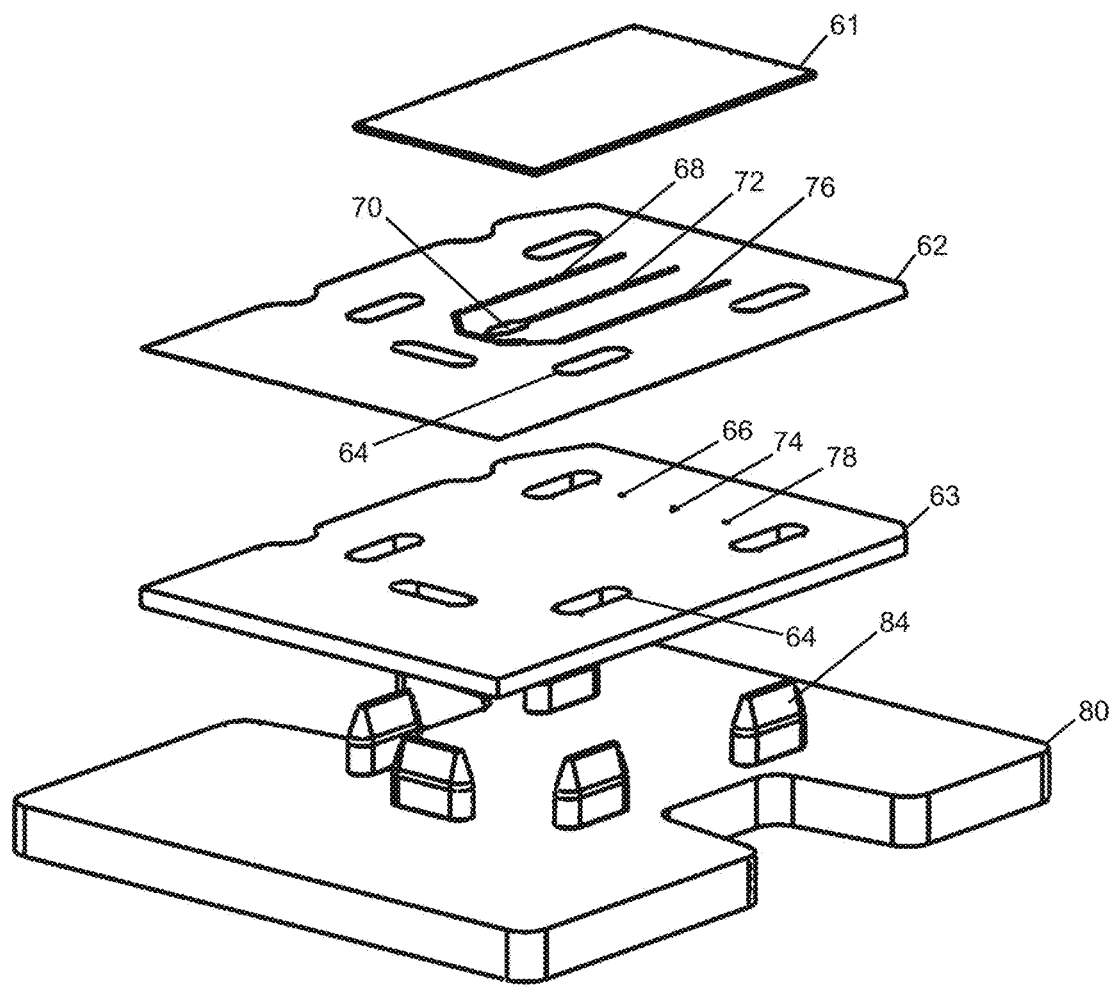
FIG. 4B is a perspective assembly view of layers of the microfluidic device of FIG. 4A arranged over an alignment fixture to facilitate alignment of the layers during fabrication, according to one embodiment of the present disclosure.

FIG. 4A is a top plan view of another microfluidic device 60 including an oil inlet 66, a buffer/reagent inlet 74, a cellular contents outlet 78, and a tissue sample chamber 70 arranged between the inlets 66, 74 and the outlet 78. FIG. 4B is a perspective assembly view of layers 61-63 of the microfluidic device 60 of FIG. 4A arranged over an alignment fixture 80 having raised protrusions 84 to facilitate alignment of the layers 61-63 during fabrication of the microfluidic device 60. As shown in FIG. 4B, the microfluidic device 60 includes a (lower) base substrate layer 63 that defines three ports (or openings) embodying the oil inlet 66, the buffer/reagent inlet 74, and the cellular contents outlet 78. The microfluidic device 60 also includes an (intermediate) adhesive channel layer 62 that defines the sample chamber 70 and multiple channel segments 68, 72, 76 each in communication with the sample chamber 70. An upper boundary of the microfluidic device 60 is formed by a cover layer 61 (e.g., a glass or polymeric slide) containing an immobilized (modified) FFPE sample (not shown), with the sample being positioned to coincide with the sample chamber 70 defined in the channel layer 62. Five oblong peripheral alignment openings 64 are arranged to permit alignment of various layers of the microfluidic device 60 during fabrication with raised protrusions of an alignment fixture. Upon assembly of the microfluidic device 60, the sample chamber 70 and channel segments 68, 72, 76 of the intermediate channel layer 62 are bounded from below by the base substrate 63, and bounded from above by the cover layer 61. Fluid communication with the channel segments 68, 72, 76 is permitted through the ports (embodying the oil inlet 66, the buffer/reagent inlet 74, and the cellular contents outlet 78) defined in the base substrate layer 63.

In operation of the microfluidic device of FIG. 4A, pulses of laser energy are directed through a surface of the sample chamber 70 (e.g., through the base substrate layer 63 or the cover layer 61) and impinged on a (modified) FFPE sample contained therein. Fluid is preferably flowed through the sample chamber 70 during laser ablation. Ablated material (preferably embodying a set of one or more whole cells) is removed and encapsulated with droplets of liquid for collection and analysis. One method for tracking a droplet containing a set of one or more cells within channels (e.g., channel segment 76) of the microfluidic device 60 or within downstream tubing is to vary the ratio of flow between the reagent/buffer and oil (which are preferably immiscible under flow conditions within the microfluidic device 60) so that the droplet sizes vary. A desired flow ratio may be established for buffer/reagent (supplied through buffer/reagent inlet 74) and oil (supplied through the oil inlet 66) in order to discretize a set of one or more cells with oil droplets in order to prevent a gradient flow of target molecules to an outlet. A resulting sequence of discrete droplets or plugs of buffer/reagent and oil are supplied through the sample chamber 70 to the cellular contents outlet 78. By assigning a flow ratio during cell extraction and changing the ratio immediately after extraction, a specific pattern of droplets will be established that indicate the beginning and end of each set of one or more cells. A pattern of droplets or plugs may be considered a "droplet barcode." Detection of these "droplet barcodes" (e.g., within the microfluidic device 60 or in tubing or conduits downstream of the microfluidic device 60) can be used to automatically distinguish between fluid volumes containing separate sets of one or more cells.

Upon exiting the microfluidic device 60, droplets may be deposited sequentially into one or more sample collection elements (e.g., well plates or other elements) and divided into separate volumes that each represent the contents of a single set of one or more cells. Each set of one or more cells may then be subjected to at least one technique (e.g., an amplification technique, a sequencing technique, or an analytical technique). Preferably, morphological and/or positional information for each set of one or more cells is stored in a memory at the time of laser ablation to permit results of the at least one technique to be related to the original spatial location of the set of cells in the immobilized sample. In certain embodiments, such information may include X, Y, and Z coordinates for each set of one or more cells relative to the original sample.

Although the phrase "set of one or more cells" is used herein, in certain embodiments, such phrase refers to a set embodying only a single cell.

Figure 5A:
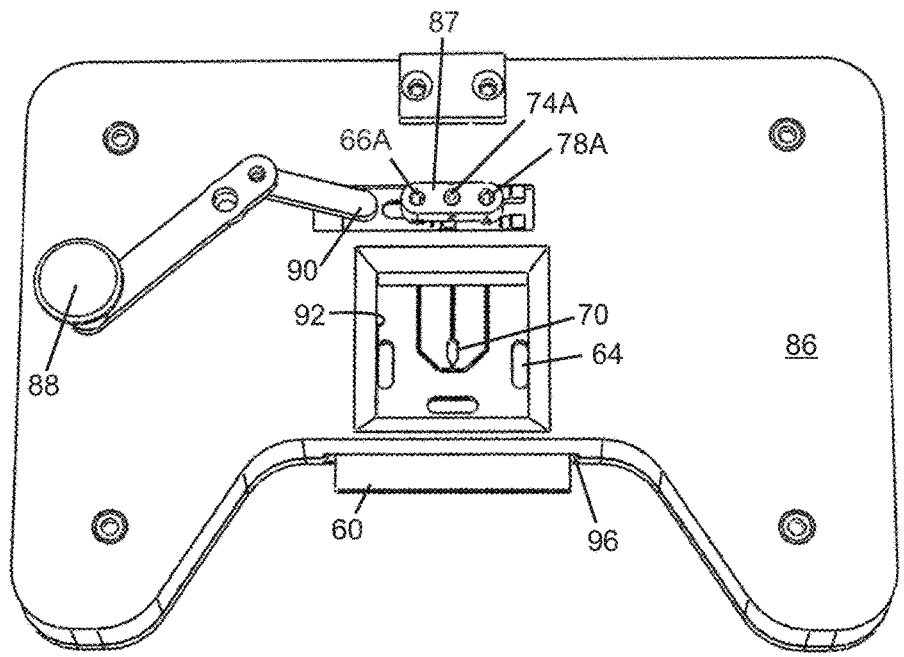
FIG. 5A is a top plan view of a microfluidic device interface having received therein a microfluidic device according to FIG. 4A.

FIG. 5A is a top plan view of a microfluidic device interface 86 having received therein a microfluidic device 60 according to FIG. 4A. The microfluidic device interface 86 includes a slot 96 permitting at least a portion of the microfluidic device 60 to be inserted therein, and includes a central window 92 permitting at least a portion of the microfluidic device 60 to receive laser energy, and to be viewed and/or imaged. A retractable manifold 87 is arranged adjacent to the window 92, with the manifold 87 including three fluid conduits 66A, 74A, 78A arranged to permit fluid communication with ports (inlets and outlet) 66, 74, 78 (shown in FIG. 4A) defined in the microfluidic device 60. A manually operable handle 88 and a mechanism 90 may be used to selectively deploy or retract the manifold 87. The entire microfluidic device interface 86 is preferably arranged to be compatible with a microscope (not shown) to permit imaging of a sample chamber 70 of the microfluidic device 60 before and during laser ablation.

Figure 5B:
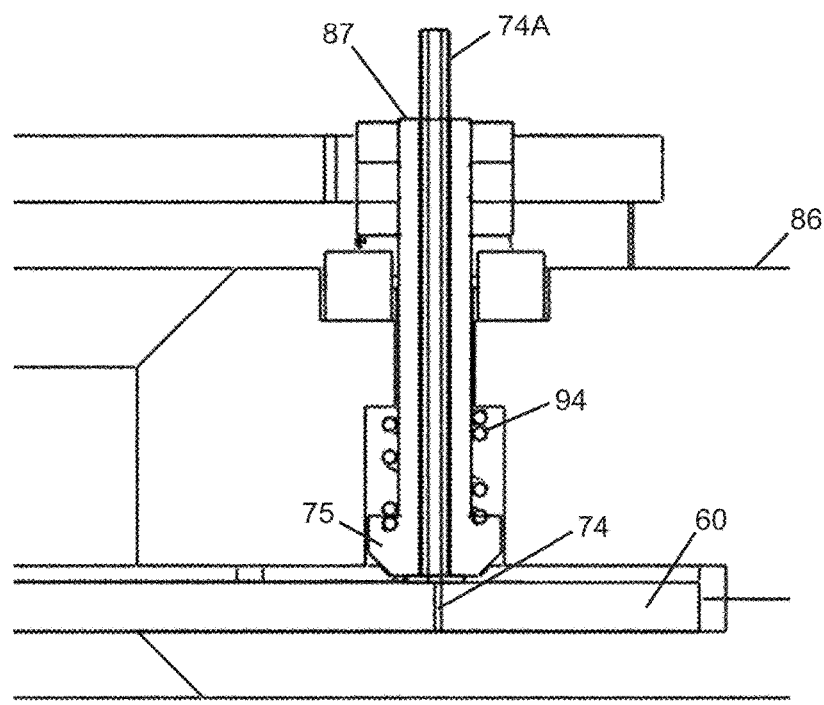
FIG. 5B is a cross-sectional view of a portion of the microfluidic device interface of FIG. 5A showing fluidic connection between a conduit of the manifold and a port of a microfluidic device, according to one embodiment of the present disclosure.

FIG. 5B is a cross-sectional view of a portion of the microfluidic device interface 86 of FIG. 5A showing fluidic connection between one conduit 74A of the manifold 87 and a port (or inlet) 74 of a microfluidic device 60. The fluid conduit 74 includes a spring-loaded tip (including a flared tip 75 pressed downward with a spring 94) configured to bias the tip 75 of the fluid conduit 74A against a surface of the microfluidic device 60, thereby avoiding leakage and limiting dead volume in a fluid connection between the microfluidic device interface 86 and the microfluidic device 60.

Figure 6:
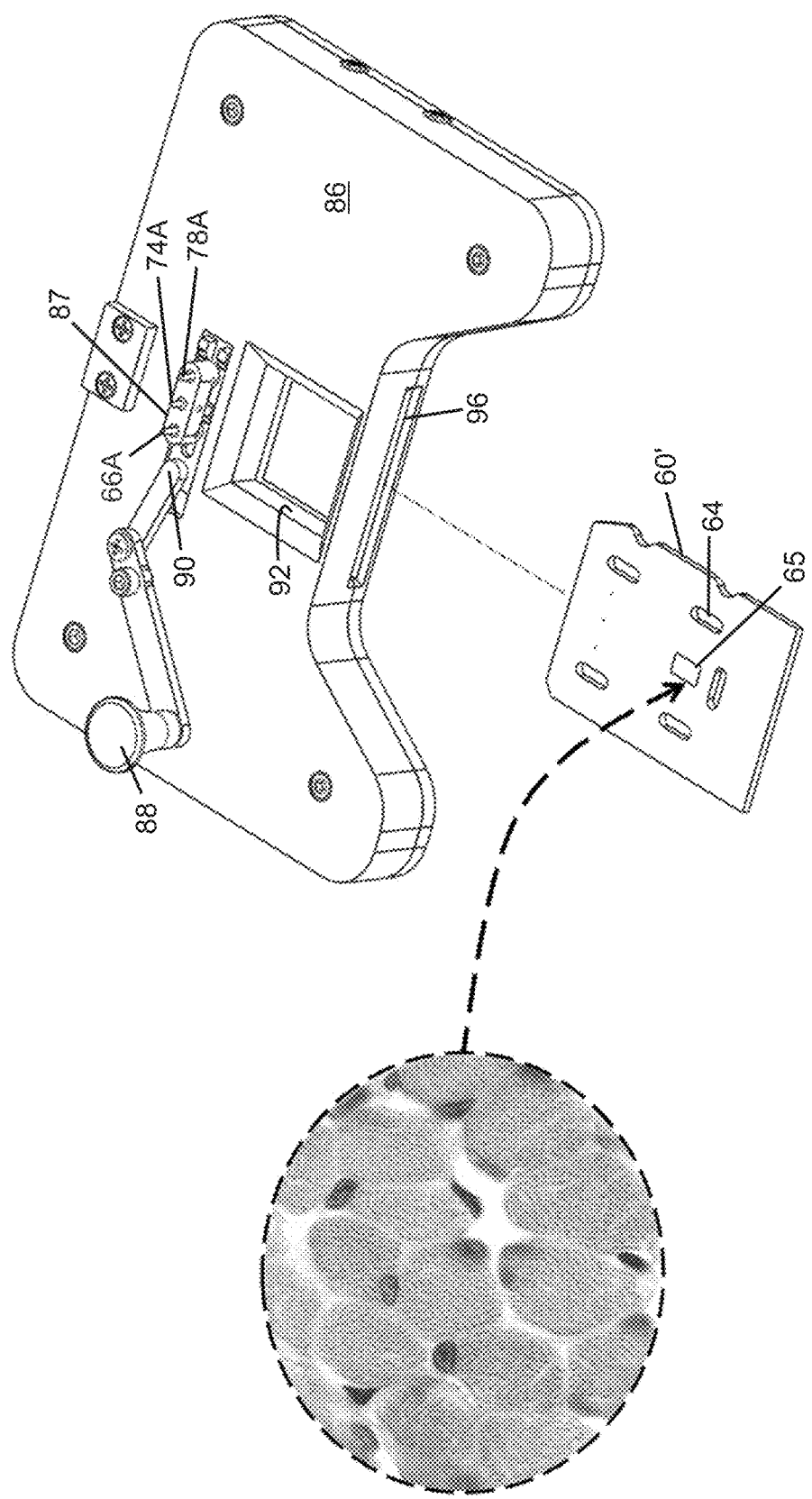
FIG. 6 is a perspective view of the microfluidic device interface of FIG. 5A arranged to receive another microfluidic device, with a magnified view of a FFPE sample arranged in a portion of the microfluidic device, according to one embodiment of the present disclosure.

FIG. 6 is a perspective view of the microfluidic device interface 86 of FIG. 5A arranged to receive another microfluidic device 60' including peripheral alignment openings 64. In certain embodiments, the microfluidic device 60' may be fabricated in part of materials characterized by little to no light transmissivity, and may include a window 65 that is transmissive of wavelengths (e.g., infrared emissions, visible light, UV emissions, or another range of wavelengths) to permit viewing and/or imaging of a sample contained in the microfluidic device 60'. FIG. 6 further shows a magnified view of a FFPE sample arranged proximate to the window 65 of the microfluidic device 60'.

Figure 7A:
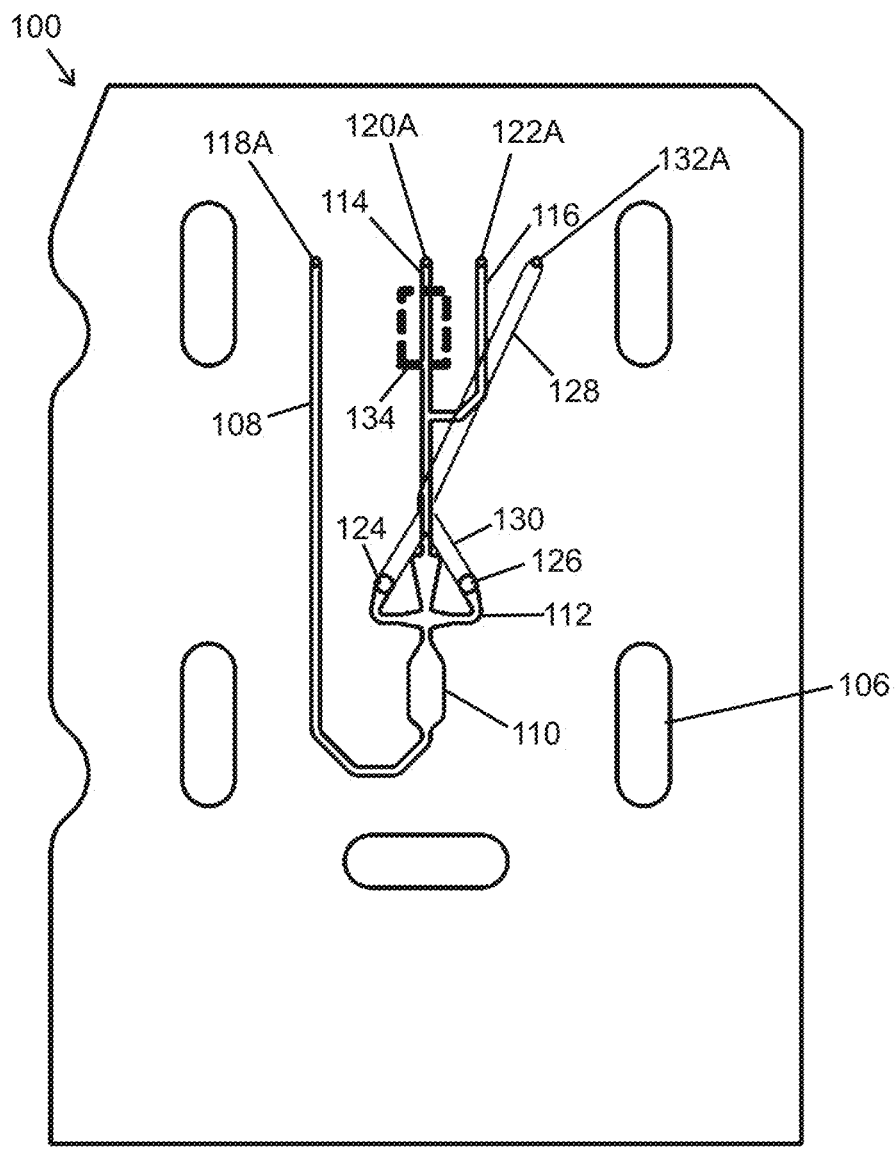
FIG. 7A is a top plan view of another microfluidic device including an oil inlet, a buffer/reagent inlet, a cellular contents outlet, and a tissue sample chamber arranged between the inlets and the outlet, and an analytical window arranged between the tissue sample chamber and the cellular contents outlet, according to one embodiment of the present disclosure.
Figure 7B:
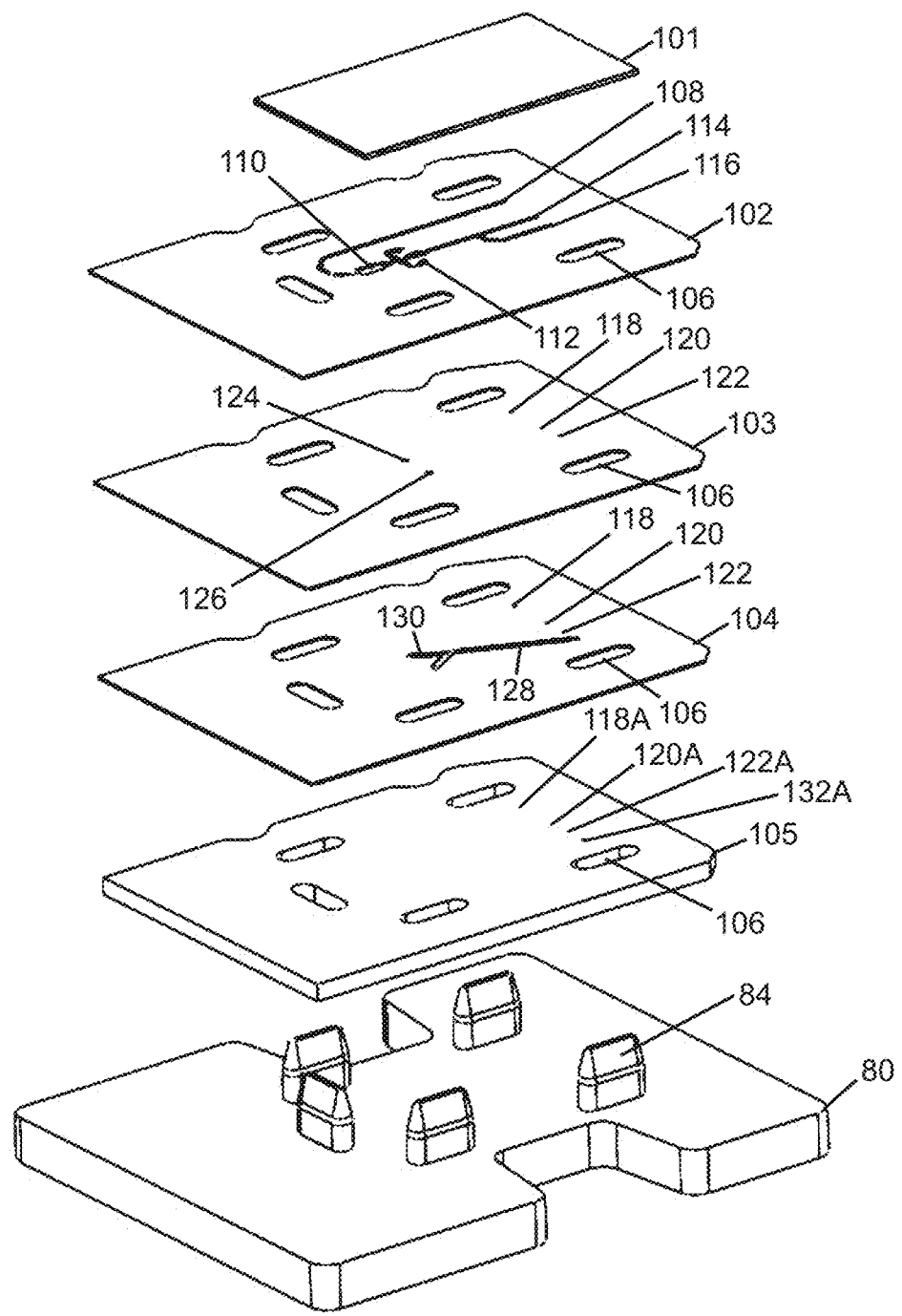
FIG. 7B is a perspective assembly view of layers of the microfluidic device of FIG. 7A arranged over an alignment fixture, according to one embodiment of the present disclosure.

FIG. 7A is a top plan view of a microfluidic device 100 including an oil inlet 132A, a buffer/reagent inlet 118A, an additional reagent inlet 122A, a cellular contents outlet 120A, and a tissue sample chamber 110. An analytical window 134 is arranged between the tissue sample chamber 110 and the cellular contents outlet 120A. Microfluidic channels 128, 108, 116, and 114 are in fluid communication with the oil inlet 132A, the buffer/reagent inlet 118A, the additional reagent inlet 122A, and the cellular contents outlet 120A, respectively. FIG. 7B is a perspective assembly view of layers 101-105 of the microfluidic device 100 of FIG. 7A arranged over an alignment fixture 80 having raised protrusions 84. As shown in FIG. 7B, the microfluidic device 100 includes a (lower) base substrate layer 105 that defines four ports embodying the oil inlet 132A, the buffer/reagent inlet 118A, the additional reagent inlet 122A, and the cellular contents outlet 120A. The microfluidic device 100 further comprises an oil channel layer 104 defining a microfluidic channel 128 and branch channels 130, a channel cap layer 103 (defining flow-through vias 118, 120, 122, 124, 126), as well as a buffer/reagent channel layer 102 that defines the sample chamber 110 and microfluidic channels 108, 112, 114, 116. A cover layer 101 contains a (modified) FFPE tissue sample (not shown) and is arranged to overlay the buffer/reagent channel layer 102. The cover layer 101 (e.g., a glass or polymeric slide) forms the upper boundary of the microfluidic device 100, with the sample being positioned to coincide with the sample chamber 110. Following assembly of the microfluidic device 100, fluid communication with the microfluidic channels 128, 108, 116, 114 is permitted through the ports (embodying the oil inlet 132A, the buffer/reagent inlet 118A, the additional reagent inlet 122A, and the cellular contents outlet 120A) defined in the base substrate layer 105. As shown in FIG. 7A, a post-analytical window 134 is provided between the sample chamber 110 and the cellular contents outlet 120A. Operation of the microfluidic device 100 of FIG. 7A is substantially similar to that of FIG. 4A, except that the post-analytical window 134 permits optical detection and/or analysis to be performed on removed sets of one or more cells following laser ablation, but before such sets of one or more cells exit the microfluidic device 100 through the outlet 120A. Five oblong peripheral alignment openings 106 are arranged to permit alignment of various layers 102-105 of the microfluidic device 100 during fabrication with raised protrusions 84 of an alignment fixture 80.

Figure 8:
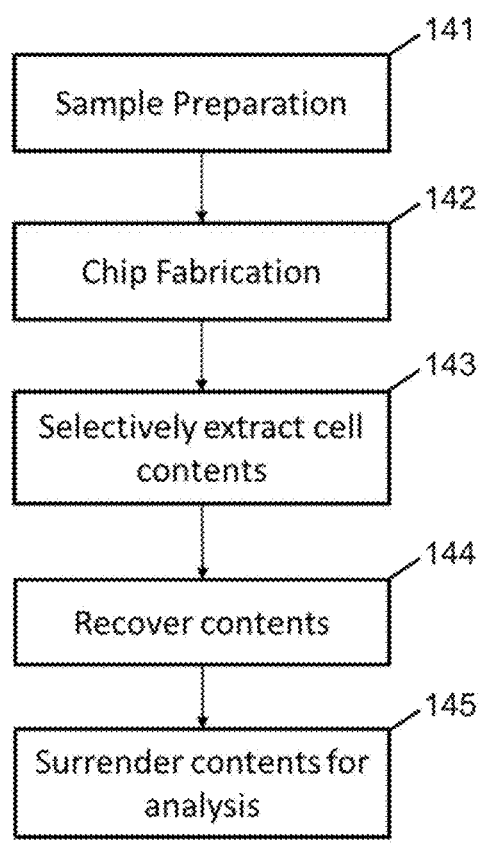
FIG. 8 is a flowchart identifying steps of a method according to one embodiment of the present disclosure.

FIG. 8 is a flowchart identifying steps of a method disclosed herein. A first step includes sample preparation 141. As described previously herein, a FFPE sample may be prepared (immobilized) on a slide and paraffin wax may be removed to yield a modified FFPE sample. A second step 142 includes microfluidic chip fabrication. A slide containing an immobilized sample may be applied to one or more layers of a microfluidic device structure, with the immobilized sample being aligned with a sample chamber, to yield a microfluidic device containing the sample therein. A third step 143 includes selective extraction of cell contents. Such step is performed by directing laser energy through a surface of a microfluidic device to impinge on a (modified) FFPE sample within the microfluidic device to separate a set of one or more cells from the sample by laser ablation. At least one fluid is flowed through the chamber to wash the removed set of one of more cells from the sample chamber. A fourth step 144 includes recovery of the set of one or more cells in at least one sample collection element. A fifth step 145 includes surrendering the contents for further processing, such as may include an amplification technique, a sequencing technique, and/or an analytical technique, wherein such techniques may be performed off-board of the microfluidic device in certain embodiments.

Figure 9:
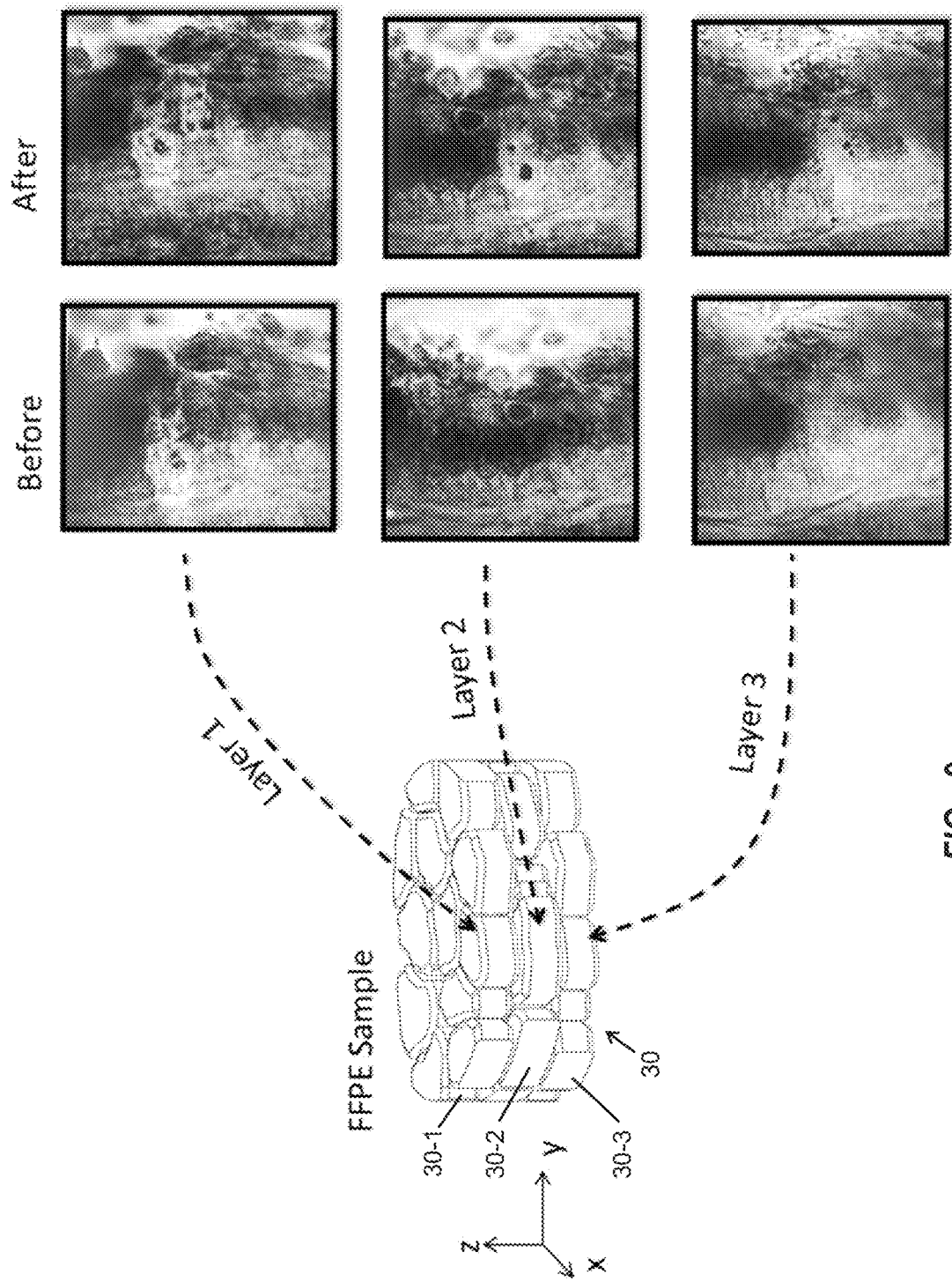
FIG. 9 schematically illustrates a three-dimensional FFPE sample including first through third layers, as well as photographs of the first, second, and third layers of the FFPE sample before and after laser ablation of cellular material.

FIG. 9 schematically illustrates a three-dimensional FFPE sample 30 including first through third layers 30-1, 30-2, 30-3, as well as photographs of first, second, and third layers of the FFPE sample before and after laser ablation of cellular material. Such figure demonstrates sequential extraction from a modified FFPE sample of single cells directly above and below each other. Such extraction is not achievable using conventional LCM techniques.

Apparatuses disclosed herein are suitable for continuous extraction of sets of one or more cells from a modified FFPE sample, while storing information indicative of morphology and/or position of the sets of one or more cells. Such apparatuses are easily scaled to high throughput and may be automated.

In certain embodiments, an apparatus for extracting at least a first set of one or more cells from an immobilized sample includes multiple elements. Such apparatus may include a microfluidic device interface arranged to receive, and provide fluidic connections to, a microfluidic device. A microfluidic device interface is preferably compatible with a microscope, and may include at least one selectively retractable manifold providing fluid connections with the microfluidic device. The apparatus may include a laser (e.g., of a multi-photon variety, such as two photon infrared laser)

arranged to direct laser energy through a surface of a microfluidic device received by the microfluidic device interface and impinge on at least a first portion of a sample immobilized within the microfluidic device for removal of at least a first set of one or more cells from the sample by laser ablation. The apparatus may include a position control element arranged to effect relative translation between the microfluidic device interface and the laser. Such position control element may include an X, Y translation stage effecting translation of the microfluidic device or the laser, and may be subject to user control via a user interface or automatic (e.g., rastered) control via computer hardware and/or software. The apparatus may include at least one liquid flow control element (e.g., pump, pressurization element, depressurization element, or the like) arranged to cause at least one liquid to flow through at least a portion of the microfluidic device and wash the removed at least a first set of one or more cells from the chamber. Preferably, at least two immiscible liquids may be supplied to the microfluidic device to permit discretization of sets of one or more cells. The apparatus may include a dispenser (e.g., dispensing nozzle, automated pipettor, or the like) arranged to dispense the removed at least a first set of one or more cells into at least one sample collection element positioned downstream of the microfluidic device. A multi-well or multi-chamber sample collection element such as a 96-well plate may be used. In certain embodiments, relative movement between the dispenser and the at least one sample collection element may be automated, such as with at least one X-Y or X-Y-Z translation element.

Upon reading the following description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. A method for extracting at least a first set of one or more cells from a sample, the method comprising:
   directing laser energy through a surface of a microfluidic device to impinge on at least a first portion of the sample immobilized within a chamber of the microfluidic device and to remove the at least a first set of one or more cells from the sample by laser ablation, wherein the sample comprises a modified formalin-fixed paraffin embedded (FFPE) sample from which paraffin has been removed; and
   washing, from the microfluidic device, the removed at least a first set of one or more cells by flowing at least one liquid through at least a portion of the microfluidic device.

2. The method of claim 1, wherein the sample comprises a thickness of at least about 10 microns.

3. The method of claim 1, further comprising removing paraffin wax from a FFPE sample retained on a cover layer of the microfluidic device to yield the modified FFPE sample, and affixing the cover layer to at least one microfluidic device layer to yield the sample immobilized within the chamber of the microfluidic device.

4. The method of claim 1, further comprising collecting the removed at least a first set of one or more cells in a sample collection element.

5. The method of claim 4, further comprising storing information representative of morphology or position, relative to the immobilized sample, of the removed at least a first set of one or more cells.

6. The method of claim 5, further comprising performing at least one technique selected from an amplification technique, a sequencing technique, or an analytical technique, utilizing the removed at least a first set of one or more cells.

7. The method of claim 6, further comprising at least one of correlating, associating, or storing results of the at least one technique with the information representative of morphology or position.

8. The method of claim 1, wherein said flowing of at least one liquid through the at least a portion of the microfluidic device comprises flowing a plurality of discrete plugs of a first liquid and a second liquid through the at least a portion of the microfluidic device, wherein the first liquid is substantially immiscible with the second liquid under flow conditions within the microfluidic device.

9. The method of claim 8, further comprising detecting the plurality of discrete plugs of the first liquid and the second liquid, and capturing or manipulating the removed at least a first set of one or more cells responsive to said detecting.

10. The method of claim 8, further comprising collecting the removed at least a first set of one or more cells in a multi-well or multi-chamber sample collection element.

11. The method of claim 1, further comprising:
   impinging laser energy on at least a second portion of the sample immobilized within the microfluidic device to remove at least a second set of one or more cells from the sample by laser ablation; and
   washing, from the microfluidic device, the removed at least a second set of one or more cells by flowing the at least one liquid through the at least a portion of the microfluidic device.

12. The method of claim 1, further comprising performing an optical detection technique on the removed at least a first set of one or more cells through an optical detection region arranged downstream of the chamber.

13. The method of claim 12, wherein the optical detection region is arranged in or on the microfluidic device.

14. A microfluidic device comprising:
   at least one fluid inlet port;
   at least one fluid outlet port;
   a sample chamber arranged between the at least one fluid inlet port and the at least one fluid outlet port, wherein the sample chamber is bounded along one surface by a cover layer; and
   a modified formalin-fixed paraffin embedded (FFPE) sample retained on the cover layer and within the sample chamber, wherein the modified FFPE sample comprises a FFPE sample from which paraffin has been removed;
   wherein at least one surface bounding the sample chamber is substantially transmissive of laser energy.

15. A method for extracting and collecting multiple sets of one or more cells from a sample, the method comprising:
   directing laser energy from a laser through a surface of a microfluidic device to impinge on a first portion of the sample immobilized within a chamber of the microfluidic device and to remove a first set of one or more cells from the sample by laser ablation, wherein the sample comprises a modified formalin-fixed paraffin embedded (FFPE) sample from which paraffin has been removed;
   washing the removed first set of one or more cells from the microfluidic device by flowing at least one liquid through the chamber;

collecting the first set of one or more cells in at least one sample collection element disposed downstream of the microfluidic device;

directing laser energy through the surface of the microfluidic device to impinge on a second portion of the sample immobilized within the chamber and to remove a second set of one or more cells from the sample by laser ablation;

washing the removed second set of one or more cells from the microfluidic device by flowing at least one liquid through the chamber; and collecting the second set of one or more cells in the at least one sample collection element disposed downstream of the microfluidic device.

16. The method of claim 15, further comprising effecting relative movement between the laser and the microfluidic device after collecting the first set of one or more cells and before directing laser energy through the surface of the microfluidic device to impinge on the second portion of the sample.

17. The method of claim 15, further comprising removing paraffin wax from a FFPE sample retained on a cover layer of the microfluidic device to yield the modified FFPE sample, and affixing the cover layer to at least one microfluidic device layer to yield the sample immobilized within the microfluidic device.

18. The method of claim 15, further comprising:

storing information representative of morphology or position, relative to the immobilized sample, of the removed first set of one or more cells; and storing information representative of morphology or position, relative to the immobilized sample, of the removed second set of one or more cells.

19. The method of claim 18, further comprising:

performing at least one first technique independently selected from an amplification technique, a sequencing technique, or an analytical technique, utilizing the removed first set of one or more cells;

performing at least one second technique independently selected from an amplification technique, a sequencing technique, or an analytical technique, utilizing the removed second set of one or more cells;

performing at least one of correlating, associating, or storing results of the at least one first technique with the information representative of morphology or position of the removed first set of one or more cells; and performing at least one of correlating, associating, or storing results of the at least one second technique with the information representative of morphology or position of the removed second set of one or more cells.

20. The method of claim 15, wherein said flowing of at least one liquid through the chamber comprises flowing a plurality of discrete plugs of a first liquid and a second liquid through the chamber, wherein the first liquid is substantially immiscible with the second liquid under flow conditions within the microfluidic device.

21. The method of claim 20, further comprising detecting the plurality of discrete plugs of the first liquid and the second liquid, and capturing or manipulating at least one of the removed first set of one or more cells or the removed second set of one or more cells responsive to said detecting.

* * * * *